(12) United States Patent
Yamamoto et al.

(10) Patent No.: US 12,091,583 B2
(45) Date of Patent: Sep. 17, 2024

(54) POLYMER COMPOUND PEELING AGENT, ADHESIVE MATERIAL, AND METHOD OF USING ADHESIVE MATERIALS

(71) Applicants: NATIONAL INSTITUTE OF ADVANCED INDUSTRIAL SCIENCE AND TECHNOLOGY, Tokyo (JP); TAT INC., Hyogo (JP)

(72) Inventors: Takahiro Yamamoto, Tsukuba (JP); Kyohei Takuno, Nishinomiya (JP); Keita Hirokawa, Nishinomiya (JP)

(73) Assignees: NATIONAL INSTITUTE OF ADVANCED INDUSTRIAL SCIENCE AND TECHNOLOGY, Tokyo (JP); TAT INC., Hyogo (JP)

( * ) Notice: Subject to any disclaimer, the term of this patent is extended or adjusted under 35 U.S.C. 154(b) by 894 days.

(21) Appl. No.: 17/058,737

(22) PCT Filed: May 8, 2020

(86) PCT No.: PCT/JP2020/018645
§ 371 (c)(1),
(2) Date: Nov. 25, 2020

(87) PCT Pub. No.: WO2020/255579
PCT Pub. Date: Dec. 24, 2020

(65) Prior Publication Data
US 2021/0261830 A1    Aug. 26, 2021

(30) Foreign Application Priority Data
Jun. 21, 2019   (JP) .................... 2019-115259

(51) Int. Cl.
C09J 11/06    (2006.01)
A45D 31/00    (2006.01)
(Continued)

(52) U.S. Cl.
CPC ............... *C09J 11/06* (2013.01); *A45D 31/00* (2013.01); *A61K 8/40* (2013.01); *A61K 8/8164* (2013.01);
(Continued)

(58) Field of Classification Search
CPC ........ C09J 11/06; C09J 4/00; C09J 2301/502; C09J 133/10; C09J 2301/408;
(Continued)

(56) References Cited

U.S. PATENT DOCUMENTS

2016/0303015 A1 * 10/2016 Kergosien ................ A61K 8/45

FOREIGN PATENT DOCUMENTS

JP        5090140 B2     12/2012
JP     2017-141187 A      8/2017
(Continued)

OTHER PUBLICATIONS

International Search Report of PCT/JP2020/18645 mailed on Aug. 11, 2020.
(Continued)

*Primary Examiner* — George R Koch
*Assistant Examiner* — Christopher C Caillouet
(74) *Attorney, Agent, or Firm* — IP Business Solutions, LLC

(57) ABSTRACT

The present invention provides a polymer compound peeling agent usable for peeling as many types of polymer compounds as possible and capable of reducing a burden required for a peeling treatment when a polymer compound having adhered to an adhesion object is peeled. The polymer compound peeling agent for peeling a polymer compound having adhered to an adhesion object contains a photoresponsive liquid crystal material having a phase structure reversibly transitioning between an isotropic phase and a liquid crystal phase due to photoisomerization based on
(Continued)

irradiation lights of different wavelengths. When the polymer compound is adhered to the adhesion object, the photoresponsive liquid crystal material is contained in the polymer compound with the phase structure set to the isotropic phase, and the phase structure of the photoresponsive liquid crystal material is allowed to transition from the isotropic phase to the liquid crystal phase by photoisomerization based on the light irradiation.

8 Claims, 7 Drawing Sheets

(51) Int. Cl.
| | | |
|---|---|---|
| *A61K 8/40* | (2006.01) | |
| *A61K 8/81* | (2006.01) | |
| *A61Q 3/04* | (2006.01) | |
| *C09J 4/00* | (2006.01) | |
| C08F 2/50 | (2006.01) | |
| C08F 222/10 | (2006.01) | |
| C08K 5/315 | (2006.01) | |

(52) U.S. Cl.
CPC .................. *A61Q 3/04* (2013.01); *C09J 4/00* (2013.01); *C08F 2/50* (2013.01); *C08F 222/1065* (2020.02); *C08K 5/315* (2013.01); *C09J 2301/502* (2020.08)

(58) Field of Classification Search
CPC .... C09J 2301/416; C09J 2433/00; C09J 5/00; C09J 201/00; A45D 31/00; A45D 29/00; A45D 29/001; A61K 8/40; A61K 8/8164; A61K 2800/81; A61K 2800/95; A61K 8/55; A61K 8/8152; A61K 8/86; A61K 8/42; A61K 8/31; A61K 8/35; A61K 8/37; A61Q 3/04; A61Q 3/00; A61Q 3/02; C08F 2/50; C08F 222/1065; C08F 2/44; C08F 2/48; C08F 220/06; C08F 220/285; C08F 222/22; C08K 5/315; C08K 5/51; A44C 15/00; A44C 15/0075; C09D 133/062; C09D 133/14; C09K 3/00
See application file for complete search history.

(56) References Cited

FOREIGN PATENT DOCUMENTS

| | | |
|---|---|---|
| JP | 2018-140945 A | 9/2018 |
| KR | 10-2017-0049552 A | 5/2017 |
| WO | 2011/074101 A1 | 6/2011 |
| WO | 2013/180196 A1 | 12/2013 |

OTHER PUBLICATIONS

Written Opinion of the International Searching Authority of PCT Application No. PCT/JP2020/18645 mailed on Aug. 11, 2020.
Korean Office Action mailed by Korean Patent Office mailed on May 10, 2022 in corresponding Korean patent application No. 10-2020-7030878.

* cited by examiner

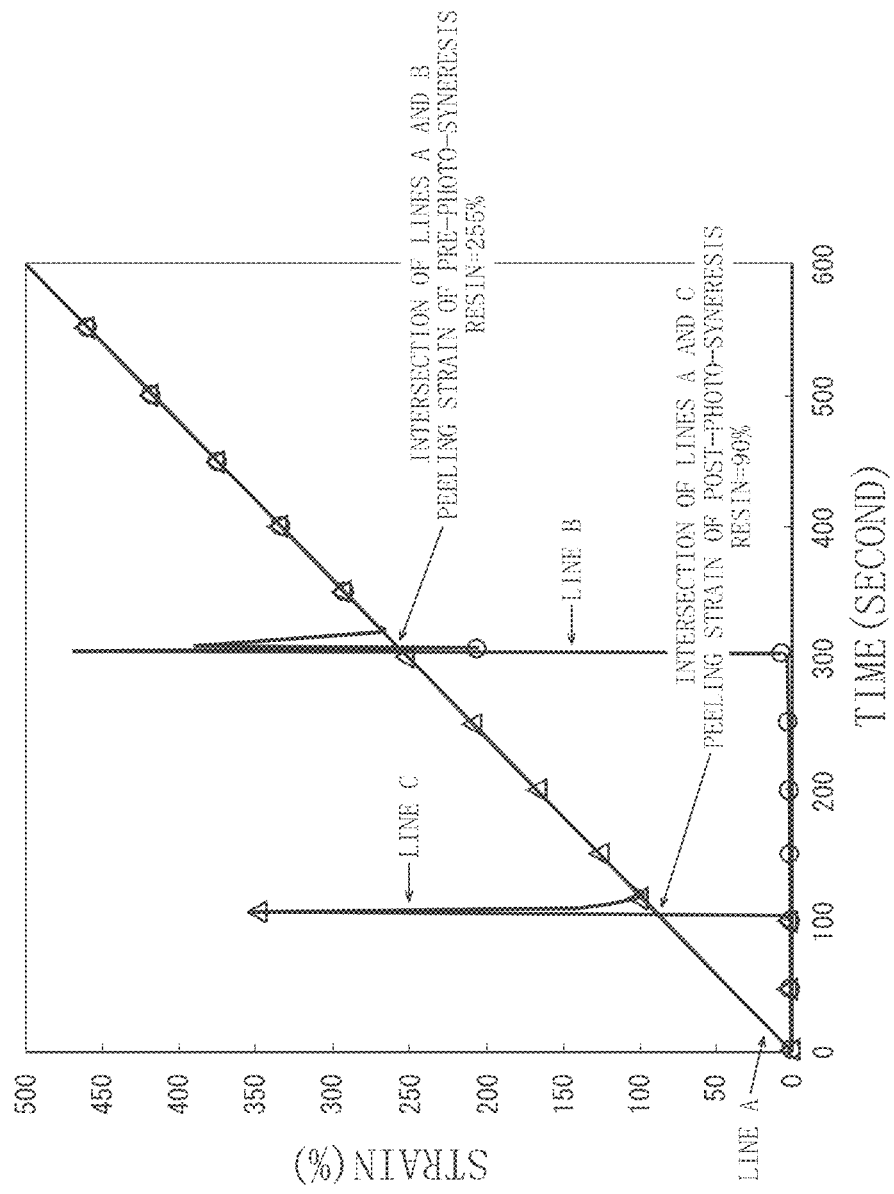
F I G. 6

POLYMER COMPOUND PEELING AGENT, ADHESIVE MATERIAL, AND METHOD OF USING ADHESIVE MATERIALS

TECHNICAL FIELD

The present invention relates to a polymer compound peeling agent, an adhesive material, and a method of using an adhesive material.

BACKGROUND ART

Adhesive materials are materials used in a state of adhering to an adhesion object. Adhesive materials are used in various forms, and examples of the usage forms include uses as coating materials and adhesives. When an adhesive material is used as a coating material, a material containing a polymerizable low-molecular-weight compound and a polymerization initiator is prepared as the coating material and is applied to an adhesion object. After the application, the polymerizable low-molecular-weight compound in the coating material is polymerized by irradiation with light such as UV (ultraviolet) light or heating, and the polymerization causes a polymer compound to adhere to the adhesion object as a hard film. As a result, the adhesion object is coated with the hard coating (polymer compound).

In recent years, such a coating technique using a polymer compound (cured film) for an adhesion object has been used for, for example, gel nails for forming artificial nails serving as cured films on the nails of hands and feet. Specifically, as described in Patent Document 1, a polymerizable low-molecular-weight compound and a photopolymerization initiator are prepared for a gel (coating material) for a gel nail, and the gel is placed on a human nail (an adhesion object) and spread over the entire nail. Subsequently, photopolymerization is performed as the polymerization treatment as described above by irradiation treatment with UV (ultraviolet) light or visible light, and an artificial nail is formed as a cured film on the human nail.

When an adhesive material is used as an adhesive, a material containing a polymerizable low-molecular-weight compound and a polymerization initiator is prepared as an adhesive and is applied to at least one of the adhesion object and an object to be bonded. The adhesion object and the object to be bonded are pressed against each other via an adhesive, and the polymerizable low-molecular-weight compound in the adhesive is then polymerized by heating or light irradiation, so that the polymerization causes a polymer compound (adhesive layer) to bond the adhesion object and the object to be bonded.

In some cases, it is desired to peel a cured film having adhered to an adhesion object from the adhesion object, or it is desired to peel at least one of the object to be bonded and the adhesion object from the adhesive layer. An example of the former case is the case of gel nails when an existing artificial nail is peeled from a human nail so as to form a new artificial nail, and an example of the latter case is the case that at least one of a coating material and a base surface for bonding the coating material is peeled from the adhesive layer. In consideration of such cases, Patent Documents 1 to 4 propose to use a composition generating a polymer compound serving as a cured film such that the polymer compound can be peeled by a specific peeling agent. Specifically, Patent Document 1 describes a composition for generating a polymer compound (artificial nail) that can be peeled by limonene serving as a peeling agent, Patent Documents 2, 3 describe a composition for generating a polymer compound (artificial nail) that can be peeled by an acidic aqueous solution serving as a peeling agent, and Patent Document 4 describes a composition for generating a polymer compound (artificial nail) that can be peeled by a highly alkaline aqueous solution serving as a peeling agent. As a result, even if the polymer compounds generated from these compositions are in a state of adhering to the adhesion object, the peeling agent corresponding to each of the polymer compounds can be brought into contact with and allowed to permeate into the polymer compound from the outside so as to peel the polymer compound from the adhesion object.

PRIOR ART DOCUMENT

Patent Document

Patent Document 1: WO2011/074101
Patent Document 2: Japanese Patent No. 5090140
Patent Document 3: Japanese Laid-Open Patent Publication No. 2017-141187
Patent Document 4: Japanese Laid-Open Patent Publication No. 2018-140945

SUMMARY OF THE INVENTION

Problem to be Solved by the Invention

However, when the polymer compound is peeled from the adhesion object in each of the cases, at least a surface of the polymer compound must be scratched by rubbing with a file to facilitate the permeation of the peeling agent before causing the peeling agent to permeate into the polymer compound from the outside, so that not only the peeling agent itself must be handled, but also a pretreatment must be performed before using the peeling agent. This increases a burden required for the peeling treatment. Particularly, to peel the object to be bonded and the adhesive layer (polymer compound) from the adhesion object, not only the treatment is required for the adhesive layer that is the polymer compound, but also a scratch reaching the adhesive layer must be made in the object to be bonded so as to facilitate the permeation of the peeling agent into the adhesive layer.

The peeling agent and the polymer compound peeled by using the peeling agent have a corresponding relationship, and the peeling agent can be used only for the limited polymer compound. Therefore, depending on the use of the polymer compound, the polymer compound may come into contact with a substance similar to the peeling agent under the usage environment, and in such a case, the polymer compound is peeled from the adhesion object regardless of the intention of a user. Therefore, depending on the use of the polymer compound, reliability cannot be ensured in terms of the state of adhesion of the polymer compound to the adhesion object.

The present invention was conceived in view of the situations, and a first object thereof is to provide a polymer compound peeling agent usable for peeling as many types of polymer compounds as possible and capable of reducing a burden required for a peeling treatment when a polymer compound having adhered to an adhesion object is peeled.

A second object is to provide an adhesive material in which the peeling agent is used.

A third object is to provide a method of using an adhesive material in which the adhesive material is used.

Means for Solving Problem

To achieve the first object, the present invention has the following configurations (1) to (3).

(1) A polymer compound peeling agent for peeling a polymer compound having adhered to an adhesion object, comprising:
- a photoresponsive liquid crystal material having a phase structure reversibly transitioning between an isotropic phase and a liquid crystal phase due to photoisomerization based on irradiation lights of different wavelengths, wherein
- when the polymer compound is adhered to the adhesion object, the photoresponsive liquid crystal material is contained in the polymer compound with the phase structure set to the isotropic phase, and wherein the phase structure of the photoresponsive liquid crystal material is allowed to transition from the isotropic phase to the liquid crystal phase by photoisomerization based on the light irradiation.

According to this configuration, even if the photoresponsive liquid crystal material is contained as the peeling agent in the polymer compound adhered to the adhesion object, the phase structure of the photoresponsive liquid crystal material is in a state of the isotropic phase (non-ordered liquid phase), the polymer compound and the photoresponsive liquid crystal material are in a miscible state, so that the photoresponsive liquid crystal material does not bleed out (float out) on the outer surface of the polymer compound. Therefore, even if the photoresponsive liquid crystal material is contained as the peeling agent in the polymer compound adhered to the adhesion object, the photoresponsive liquid crystal material is not interposed between the adhesion object and the polymer compound, and the state of adhesion of the polymer compound to the adhesion object is maintained. On the other hand, when the phase structure of the photoresponsive liquid crystal material changes from the isotropic phase to the liquid crystal phase (ordered liquid phase) due to photoisomerization based on the light irradiation, the polymer compound and the photoresponsive liquid crystal material are brought into a phase-separation state, so that the photoresponsive liquid crystal material bleeds out (floats out) on the outer surface of the polymer compound. Therefore, the photoresponsive liquid crystal material is interposed between the adhesion object and the polymer compound, and the polymer compound is made peelable from the adhesion object. As described above, even if the photoresponsive liquid crystal material is contained in the polymer compound, a situation can be created such that the polymer compound can basically be adhered to the adhesion object, and on the other hand, the polymer compound can be peeled from the adhesion object (the photoresponsive liquid crystal material is bled out on the outer surface of the polymer compound) by simply bringing the photoresponsive liquid crystal material into the liquid crystal phase through photoisomerization based on the light irradiation, so that not only the need for consciously handling the peeling agent itself can be eliminated, but also the pretreatment such as rubbing and scratching the surface of the polymer compound with a file can be omitted. Therefore, when the polymer compound adhered to the adhesion object is peeled, a burden required for the peeling treatment can be reduced.

Moreover, in this case, basically regardless of what kind of the polymer compound is used, the photoresponsive liquid crystal material exhibits the syneresis and non-syneresis actions with respect to the polymer compound and therefore can be used for peeling as many types of polymer compounds as possible. As a result, the polymer compound can be selected from a number of types of polymer compounds depending on intended use so that the reliability of adhesion of the polymer compound to the adhesion object can be improved.

(2) Under the configuration of (1), when the photoresponsive liquid crystal material is irradiated with the irradiation light that is visible light, the phase structure of the photoresponsive liquid crystal material transitions to the isotropic phase, and when the photoresponsive liquid crystal material is irradiated with the irradiation light that is UV (ultraviolet) light, the phase structure of the photoresponsive liquid crystal material transitions to the liquid crystal phase.

According to this configuration, even though the polymer compound adhered to the adhesion object is exposed to visible light in daily life, and the photoresponsive liquid crystal material (the peeling agent) contained in the polymer compound is irradiated with visible light, the phase structure of the photoresponsive liquid crystal material is maintained in the isotropic phase, and the adhesiveness of the polymer compound adhered to the adhesion object can be prevented from decreasing in daily life. On the other hand, when the photoresponsive liquid crystal material in the polymer compound is irradiated with UV (ultraviolet) light that is special light in daily life, the polymer compound is made peelable from the adhesion object (the photoresponsive liquid crystal material bleeds out on the outer surface of the polymer compound). Therefore, when it is necessary to peel the polymer compound from the adhesion object while the adhesiveness of the polymer compound to the adhesion object is ensured in daily life, the peeling can accurately be performed.

(3) A polymer compound peeling agent for peeling a polymer compound having adhered to an adhesion object, comprising:
- a liquid crystal material having a phase structure reversibly transitioning between an isotropic phase and a liquid crystal phase based on temperature adjustment, wherein
- when the polymer compound is adhered to the adhesion object, the liquid crystal material is contained in the polymer compound with the phase structure set to the isotropic phase, and wherein the phase structure of the photoresponsive liquid crystal material is allowed to transition from the isotropic phase to the liquid crystal phase based on the temperature adjustment.

According to this configuration, even if the liquid crystal material is contained as the peeling agent in the polymer compound adhered to the adhesion object, the phase structure of the liquid crystal material is in a state of the isotropic phase (non-ordered liquid phase), the polymer compound and the liquid crystal material are in a miscible state, so that the liquid crystal material does not bleed out (float out) on the outer surface of the polymer compound. Therefore, even if the liquid crystal material is contained as the peeling agent in the polymer compound adhered to the adhesion object, the liquid crystal material is not interposed between the adhesion object and the polymer compound, and the state of adhesion of the polymer compound to the adhesion object is maintained. On the other hand, when the phase structure of the liquid crystal material changes from the isotropic phase to the liquid crystal phase (ordered liquid phase) based on the temperature adjustment, the polymer compound and the liquid crystal material are brought into a phase-separation state, so that the liquid crystal material bleeds out (floats out) on the outer surface of the polymer compound. Therefore, the liquid crystal material is interposed between the adhesion object and the polymer compound, and the polymer compound is made peelable from the adhesion object. As described above, even if the liquid crystal material is contained in the polymer compound before use, a situation can be created such that the polymer compound can basically be adhered to the adhesion object, and on the other hand, the polymer compound can be peeled from the adhesion object (the liquid crystal material is bled out on the outer surface of the polymer compound) by simply bringing the liquid crystal material into the liquid crystal phase through the temperature adjustment, so that not only the need for consciously handling the peeling agent itself can be eliminated, but also the pretreatment such as rubbing and scratching the surface of the polymer compound with a file can be omitted. Therefore, when the polymer compound adhered to the adhesion object is peeled, a burden required for the peeling treatment can be reduced.

Obviously, even in this case, basically regardless of what kind of the polymer compound is used, the liquid crystal material exhibits the syneresis and non-syneresis actions with respect to the polymer compound and therefore can be used for peeling as many types of polymer compounds as possible.

To achieve the second object, the present invention has the following configurations (4) to (7).

(4) An adhesive material containing one or more types of polymerizable low-molecular-weight compounds turned into a polymer compound by a polymerization treatment, wherein the adhesive material further contains a photoresponsive liquid crystal material having a phase structure allowed to reversibly transition between an isotropic phase and a liquid crystal phase due to photoisomerization based on irradiation lights of different wavelengths, under the state in which the phase structure is set to the isotropic phase, wherein when the one or more types of the polymerizable low-molecular-weight compounds are turned into a polymer compound by a polymerization treatment, the phase structure of the photoresponsive liquid crystal material is maintained in the state of the isotropic phase, and wherein the phase structure of the photoresponsive liquid crystal material is allowed to transition from the isotropic phase to the liquid crystal phase by photoisomerization based on the irradiation light.

According to this configuration, even if the photoresponsive liquid crystal material is contained as the peeling agent in the adhesive material, the photoresponsive liquid crystal material is maintained in the state of the isotropic phase when the one or more types of the polymerizable low-molecular-weight compounds are turned into the polymer compound by the polymerization treatment, and therefore, the photoresponsive liquid crystal material does not bleed out to the outer surface of the polymer compound, so that the polymer compound can accurately be adhered to the adhesion object. On the other hand, when the polymer compound is peeled from the adhesion object, the phase structure of the photoresponsive liquid crystal material can be changed from the isotropic phase to the liquid crystal phase by photoisomerization based on the irradiation light, and the polymer compound and the photoresponsive liquid crystal material can be brought into a phase-separation state by the transition to the liquid crystal phase so as to cause the photoresponsive liquid crystal material to bleed out on the outer surface of the polymer compound (between the polymer compound and the adhesion object). Therefore, under the situation where the polymer compound can basically be adhered to the adhesion object, the polymer compound can be made peelable from the adhesion object through the syneresis action of the photoresponsive liquid crystal material simply by photoisomerization based on the irradiation light, and the burden required for the peeling treatment can be reduced.

Moreover, in this case, basically regardless of what kind of the polymer compound is used, the photoresponsive liquid crystal material exhibits the syneresis and non-syneresis actions with respect to the polymer compound and therefore can be used for peeling as many types of polymer compounds as possible. As a result, many compounds can be used as the polymerizable low-molecular-weight compound contained in the adhesive material, and the compound can be selected from a number of polymerizable low-molecular-weight compounds depending on intended use so that the reliability of adhesion of the polymer compound to the adhesion object can be improved.

Moreover, in this case, since the polymerizable low-molecular-weight compound is polymerized when the polymer compound to be adhered to the adhesion object is synthesized, the polymerizable low-molecular-weight compound and the photoresponsive liquid crystal material can easily be mixed before the polymerization, and the mixture can be applied to the adhesion object. Therefore, facilitation of production of the adhesive material and good usability of the adhesive material can be ensured.

(5) Under the configuration of (4), when the photoresponsive liquid crystal material is irradiated with the irradiation light for photoisomerization that is visible light, the phase structure of the photoresponsive liquid crystal material transitions to the isotropic phase, and when the photoresponsive liquid crystal material is irradiated with the irradiation light for photoisomerization that is UV (ultraviolet) light, the phase structure of the photoresponsive liquid crystal material transitions to the liquid crystal phase, and the one or more types of the polymerizable low-molecular-weight compounds turn into a polymer compound at the time of irradiation with the visible light for the polymerization treatment.

According to this configuration, the photoresponsive liquid crystal material can maintain the phase structure in the isotropic phase even in daily life under visible light, and the adhesiveness of the polymer compound to the adhesion object can be prevented from decreasing. On the other hand, only when the photoresponsive liquid crystal material in the polymer compound is irradiated with UV (ultraviolet) light that is special light in daily life, the phase structure of the photoresponsive liquid crystal material can be changed to the liquid crystal phase so as to peel the polymer compound from the adhesion object (to cause the photoresponsive liquid crystal material to bleed out on the outer surface of the polymer compound). Therefore, when it is necessary to peel the polymer compound from the adhesion object while the adhesiveness of the polymer compound to the adhesion object is basically ensured in daily life, the peeling can accurately be performed.

Moreover, in this case, although visible light is used as the irradiation light for the polymerization treatment when the one or more types of the polymerizable low-molecular-weight compounds are polymerized into the polymer compound, the phase structure of the photoresponsive liquid crystal material is maintained in the isotropic phase when the photoresponsive liquid crystal material contained in the polymer compound is irradiated with the visible light, and therefore, the phase structure of the photoresponsive liquid crystal material is not changed to the liquid crystal phase by the visible light, so that the isotropic phase is kept maintained (non-syneresis state). Therefore, even when visible light is used as the irradiation light at the time of polymerization of the one or more types of the polymerizable low-molecular-weight compounds, the polymer compound can accurately be adhered to the adhesion object.

(6) An adhesive material to be adhered to an adhesion object, comprising:
a solvent,
a polymer compound dissolved in the solvent and becoming adhesive while forming a film on a surface of the adhesion object when the solvent volatilizes; and
a photoresponsive liquid crystal material that has a phase structure allowed to reversibly transition between an isotropic phase and a liquid crystal phase due to photoisomerization based on irradiation lights of different wavelengths and that is in an isotropic phase state when mixed with the polymer compound and the solvent, wherein
the photoresponsive liquid crystal material is maintained in the isotropic phase state while the polymer compound is adhered to the adhesion object, and wherein the phase structure of the photoresponsive liquid crystal material is allowed to transition from the isotropic phase to the liquid crystal phase based on the irradiation light for photoisomerization.

According to this configuration, after the photoresponsive liquid crystal material is mixed with the solvent in which the polymer compound is dissolved, the mixture can be applied to the adhesion object, and a polymer compound film can be generated from the mixture by volatilizing the solvent so that the polymer compound can be adhered to the adhesion object. On the other hand, by bringing the photoresponsive liquid crystal material into the liquid crystal phase by photoisomerization based on the light irradiation (by a syneresis action based on a phase separation state), the polymer compound can be peeled from the adhesion object.

(7) Under any of the configurations (4) to (6),
the adhesive material is used as a main component of a gel for a gel nail, and
the adhesion object is a human nail.

According to this configuration, the coating material can be applied onto a human nail and the polymer compound of the coating material can be adhered to a surface of the nail. Therefore, the polymer compound can form an artificial nail as a cured film. On the other hand, the phase structure of the photoresponsive liquid crystal material is changed from the isotropic phase to the liquid crystal phase simply by irradiating the artificial nail with light so that the photoresponsive liquid crystal material can be bled out between the artificial nail, which is the polymer compound, and a human nail surface. Therefore, even when the adhesive material is used as a main component of a gel for a gel nail, the artificial nail can accurately be peeled from the human nail surface.

Moreover, since the non-syneresis and syneresis actions of the photoresponsive liquid crystal material used for adhesion/peeling of the artificial nail (polymer compound) to/from the adhesion object can be generated in many types of polymer compounds, an appropriate polymer compound or a polymerizable low-molecular-weight compound generating the appropriate polymer compound can be selected without selecting a polymer compound for which substances under the usage environment of the artificial nail (e.g., water, acidic water, alkaline water, etc.) act as a peeling agent. Therefore, the reliability of adhesion of the artificial nail to the human nail surface can be improved.

To achieve the third object, the present invention has the following configurations (8) to (12).

(8) A method of using an adhesive material, wherein
an adhesive material is prepared by mixing one or more types of polymerizable low-molecular-weight compounds, a polymerization initiator, and a photoresponsive liquid crystal material having a phase structure in an isotropic phase state and having the phase structure allowed to transition from an isotropic phase to a liquid crystal phase by photoisomerization based on light irradiation, wherein
when the adhesive material is adhered to the adhesion object a polymer compound is generated by polymerizing the one or more types of the polymerizable low-molecular-weight compounds after the adhesive material is placed on the adhesion object, and wherein
when the polymer compound is peeled from the adhesion object, the phase structure of the photoresponsive liquid crystal material is changed from the isotropic phase to the liquid crystal phase by photoisomerization based on the light irradiation.

According to this configuration, the adhesion/peeling of the polymer compound to/from the adhesion object can accurately be performed by using the adhesive material according to (4) described above.

(9) A method of using an adhesive material, wherein
an adhesive material is prepared that contains a solvent, a polymer compound dissolved in the solvent and becoming adhesive while forming a film on an adhesion object when the solvent volatilizes, and a photoresponsive liquid crystal material mixed with the polymer compound in the solvent and having a phase structure in an isotropic phase state, wherein
when the adhesive material is adhered to the adhesion object, the solvent is volatilized after the adhesive material is placed on the adhesion object, and wherein
when the polymer compound is peeled from the adhesion object, the phase structure of the photoresponsive liquid crystal material is changed from the isotropic phase to the liquid crystal phase by photoisomerization based on the light irradiation.

According to this configuration, the adhesion/peeling of the polymer compound t/from the adhesion object can accurately be performed by using the adhesive material according to (6) described above.

(10) Under the configuration of (8) or (9),
the adhesive material is a main component of a gel for a gel nail, and
the adhesion object is a human nail.

According to this configuration, the artificial nail (polymer compound) can accurately be formed on and peeled from a human nail surface (adhesion object) by using the adhesive material according to (7) described above. In this case, when the artificial nail is peeled from the human nail surface, it is only necessary to irradiate the artificial nail with light to change the phase structure of the photoresponsive liquid crystal material to the liquid crystal phase, and therefore, the needs for not only consciously handling the peeling agent itself but also performing a pretreatment before the peeling treatment can be eliminated, so that a burden required for the peeling treatment can be reduced.

(11) Under the configuration of (8) or (9),
the adhesive material is a main component of a paint, and
the adhesion object is an application surface.

According to this configuration, if the main component of the paint (coating material) is applied to the application surface, a coating film can be formed on the application surface from the polymer compound. On the other hand, when the coating film is peeled, it is only necessary to irradiate the coating film with light to change the phase structure of the photoresponsive liquid crystal material to the liquid crystal phase, and therefore, the needs for not only consciously handling the peeling agent itself but also performing a pretreatment before the peeling treatment can be eliminated, so that a burden required for the peeling treatment can be reduced. Moreover, in this case, although the coating film formed on the application surface is transparent, the coating film becomes opaque when the phase structure of the photoresponsive liquid crystal material is changed to the liquid crystal phase so as to peel the coating film, so that whether the light irradiation performed at the time of the peeling treatment is accurately performed can visually be confirmed.

(12) Under the configuration of (8) or (9),
when an object to be bonded is bonded to the adhesion object via the adhesive material, after the adhesive material is applied to at least one of the adhesion object and the object to be bonded, the adhesion object and the object to be bonded are pressed against each other to generate the polymer compound between the adhesion object and the object to be bonded, and
when the polymer compound is peeled from at least one of the adhesion object and the object to be bonded, an irradiation light for transitioning the phase structure of the photoresponsive liquid crystal material from the isotropic phase to the liquid crystal phase is applied between the adhesion object and the object to be bonded, or after at least one of the adhesion object and the object to be bonded is made up of a transparent member in advance, the irradiation light is applied to the transparent member.

According to this configuration, even when the adhesion object and the object to be bonded are bonded via the polymer compound, and the polymer compound is peeled from at least one of the adhesion object and the object to be bonded, the irradiation light for transitioning the phase structure of the photoresponsive liquid crystal material from the isotropic phase to the liquid crystal phase can be applied between the adhesion object and the object to be bonded, or after at least one of the adhesion object and the object to be bonded is made up of a transparent member in advance, the irradiation light can be applied to the transparent member, so as to cause the photoresponsive liquid crystal material to bleed out to the outer surface of the polymer compound, so that the polymer compound can be peeled from at least one of the adhesion object and the object to be bonded. Moreover, even in this case, the needs for not only consciously handling the peeling agent itself but also performing a pretreatment before the peeling treatment can be eliminated, so that a burden required for the peeling treatment can be reduced.

Effect of the Invention

The present invention can provide a polymer compound peeling agent usable for peeling as many types of polymer compounds as possible and capable of reducing a burden required for a peeling treatment when a polymer compound having adhered to an adhesion object is peeled, an adhesive material, and a method of using an adhesive material.

BRIEF DESCRIPTION OF DRAWINGS

FIG. 6 is a diagram showing adhesion properties (peeling properties) of the resins obtained from the composition composed of the photopolymerizable mixture 3 and the photo-syneresis liquid peeling agent 3, before photo-syneresis (pre-photo-syneresis resin) and after photo-syneresis (post-photo-syneresis resin).

MODES FOR CARRYING OUT THE INVENTION

Figure 1:
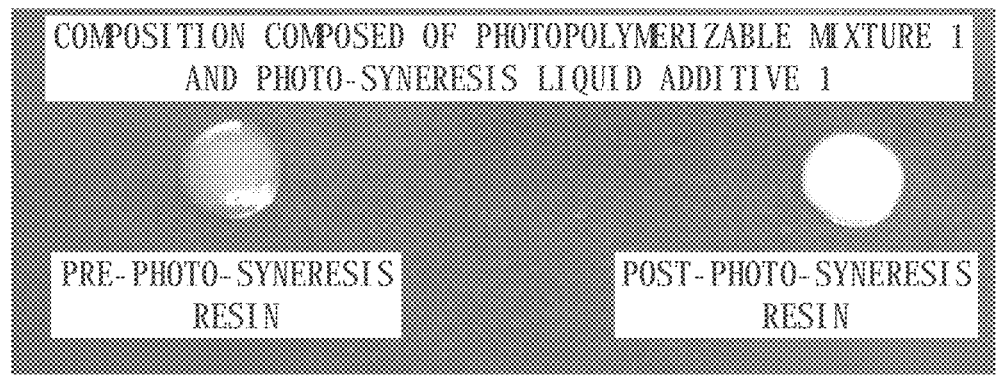
FIG. 1 is a photographic diagram showing a state of resins obtained from a composition composed of a photopolymerizable mixture 1 and a photo-syneresis liquid peeling agent 1, before photo-syneresis (pre-photo-syneresis resin) and after photo-syneresis (post-photo-syneresis resin).

An embodiment of the present invention will now be described.

1. An adhesive material according to this embodiment contains one or more types of polymerizable low-molecular-weight compounds, a polymerization initiator, and a photoresponsive liquid crystal material serving as a polymer compound peeling agent. The case of using the adhesive material as a coating material will be specifically described as an example.

(1) One or more types of the polymerizable low-molecular-weight compounds have a role of turning into the polymer compound through polymerization thereof. This is for the purpose of generating the polymer compound serving as a hard film adhered to an adhesion object.

(i) The polymerizable low-molecular-weight compound is preferably in a range of 9 wt % to 85 wt % with respect to the entire coating material, more preferably 29 wt % to 75 wt % from the viewpoint of accurate phase separation from the polymer compound when the photoresponsive liquid crystal material is changed to a liquid crystal phase by light irradiation, further preferably 39 wt % to 65 wt % from the viewpoint of maintaining the hardness of the film.

(ii) various compounds can be used as the polymerizable low-molecular-weight compound. As described later, this is because the action of the photoresponsive liquid crystal material serving as the peeling agent (non-syneresis and syneresis actions described later) can be applied to many polymer compounds. As a result, attention can be focused on characteristics such as adhesiveness of the polymer compound generated through the polymerization of each of the polymerizable low-molecular-weight compounds so as to utilize the characteristics.

(iii) Specifically, for the polymerizable low-molecular-weight compound, a polymerizable low-molecular-weight compound having one polymerizable group such as a (meth) acryloyl group in the structure (monofunctional monomer) or a polymerizable low-molecular-weight compound having two or more polymerizable groups such as a (meth)acryloyl group in the structure (polyfunctional monomer) can be used alone, or two or more types of each of the compounds can be mixed and used.

(iii-1) Examples of the monofunctional monomer include methyl (meth)acrylate, ethyl (meth)acrylate, 2-ethylhexyl (meth)acrylate, 2-hydroxyethyl (meth)acrylate, 2-hydroxypropyl (meth)acrylate, 2-Hydroxyethyl (meth)acrylamide, isobornyl (meth)acrylate, polyethylene glycol methyl ether (meth)acrylate, etc.

(iii-2) Examples of the polyfunctional monomer include diurethane di(meth)acrylate, bisphenol A ethoxylate di(meth)acrylate, ethylene glycol di(meth)acrylate, triethylene glycol di(meth)acrylate, tetraethylene glycol di(meth)acrylate, propylene glycol di(meth)acrylate, trimethylolpropane tri(meth)acrylate, tetramethylolpropane tetra(meth)acrylate, pentaerythritol (meth)acrylate, pentaerythritol tetra(meth)acrylate, dipentaerythritol penta(meth)acrylate, dipentaerythritol hexa(meth)acrylate, cardo epoxy di(meth)acrylate, N,N'-methylenebisacrylamide etc. However, the present invention is not limited to these examples.

Particularly, from the viewpoint that after turning into a polymer compound, the polymer compound does not inhibit the syneresis action of the photoresponsive liquid crystal material described later, methyl (meth)acrylate, ethyl (meth) acrylate, isobornyl (meth)acrylate, polyethylene glycol methyl ether (meth)acrylate, diurethane di(meth)acrylate, bisphenol A ethoxylate di(meth)acrylate, etc. are preferably used. However, the present invention is not limited to these examples.

(iv) The polymerizable low-molecular-weight compound is used instead of a polymer compound in the coating material so as to facilitate mixing with the photoresponsive liquid crystal material and facilitate application of the mixture to the adhesion object.

(v) Light irradiation or heating is used for the polymerization of the polymerizable low-molecular-weight compound. When the polymerizable low-molecular-weight compound is polymerized by light irradiation, irradiation light used is light capable of not only turning the polymerizable low-molecular-weight compound into the polymer compound through polymerization in the presence of a photopolymerization initiator, but also transitioning or maintaining the phase structure of the photoresponsive liquid crystal material into or at the isotropic phase. Such light is used so as not to impair the function of the photoresponsive liquid crystal material (details will be described later). Specifically, visible light is used as the irradiation light. The visible light having a wavelength range of 400 to 600 nm are preferable, and the visible light having the wavelength of 405 nm is more preferable. This is because the light of 405 nm is currently widely used as the light for curing a gel in applications such as gel nails described later, and existing light sources can be used. This is also because the influence on a contact object (particularly, the human body) can be reduced as compared to when UV (ultraviolet) light is applied.

(2) The polymerization initiator initiates the polymerization of the polymerizable low-molecular-weight compound to synthesize the polymer compound. For the polymerization initiator, various polymerization initiators generally used for thermal polymerization by heating and photopolymerization by light irradiation can appropriately be used depending on a polymerization temperature and irradiation light wavelength, and by using these initiators, polymerization reactions generally used for synthesis of polymer compounds such as radical polymerization, cation polymerization, and anion polymerization can be performed as the polymerization of the polymerizable low-molecular-weight compound.

Specifically, examples of the initiator used for thermal polymerization include 2,2'-azodiisobutyronitrile, 2,2'-azobis(2-methylbutyronitrile), dicyandiamide, etc.

Examples of the initiator used for photopolymerization include phenylbis(2,4,6-trimethylbenzoyl)phosphine oxide, tri-p-tolylsulfonium trifluoromethanesulfonate, 2-nitrobenzyl cyclohexylcarbamate etc. However, the present invention is not limited to these examples.

The polymerization initiator is preferably in a range of 1 wt % to 5 wt % with respect to the entire coating material so as to accurately initiate the polymerization of the polymerizable low-molecular-weight compound by heating or light irradiation. Trhe concentration exceeding 5 wt % is not preferable since the polymer compound generated by the polymerization may be reduced in molecular weight and the adhesive strength etc. may be lowered.

(3) The photoresponsive liquid crystal material serving as a peeling agent is mixed with the polymerizable low-molecular-weight compound and the polymerization initiator described above in the coating material before use. This is because after the polymerizable low-molecular-weight compound is polymerized to generate the polymer compound, the adhesion/peeling of the polymer compound to/from the adhesion object is adjusted.

(i) The photoresponsive liquid crystal material has a function of phase transition between a liquid crystal phase (ordered liquid phase) and an isotropic phase (non-ordered liquid phase) as a basic function. The photoresponsive liquid crystal material has a liquid crystal phase-isotropic phase transition temperature (hereinafter, phase transition temperature) $T_{LC-1}$ as a phase transition reference temperature between the liquid crystal phase and the isotropic phase, and when the temperature (operating temperature) of the photoresponsive liquid crystal material is lower than the phase transition temperature $T_{LC-1}$, the photoresponsive liquid crystal material has the liquid crystal phase, and when the temperature (operating temperature) of the photoresponsive liquid crystal material is higher than the phase transition temperature $T_{LC-1}$ the photoresponsive liquid crystal material has the isotropic phase.

Figure 7:
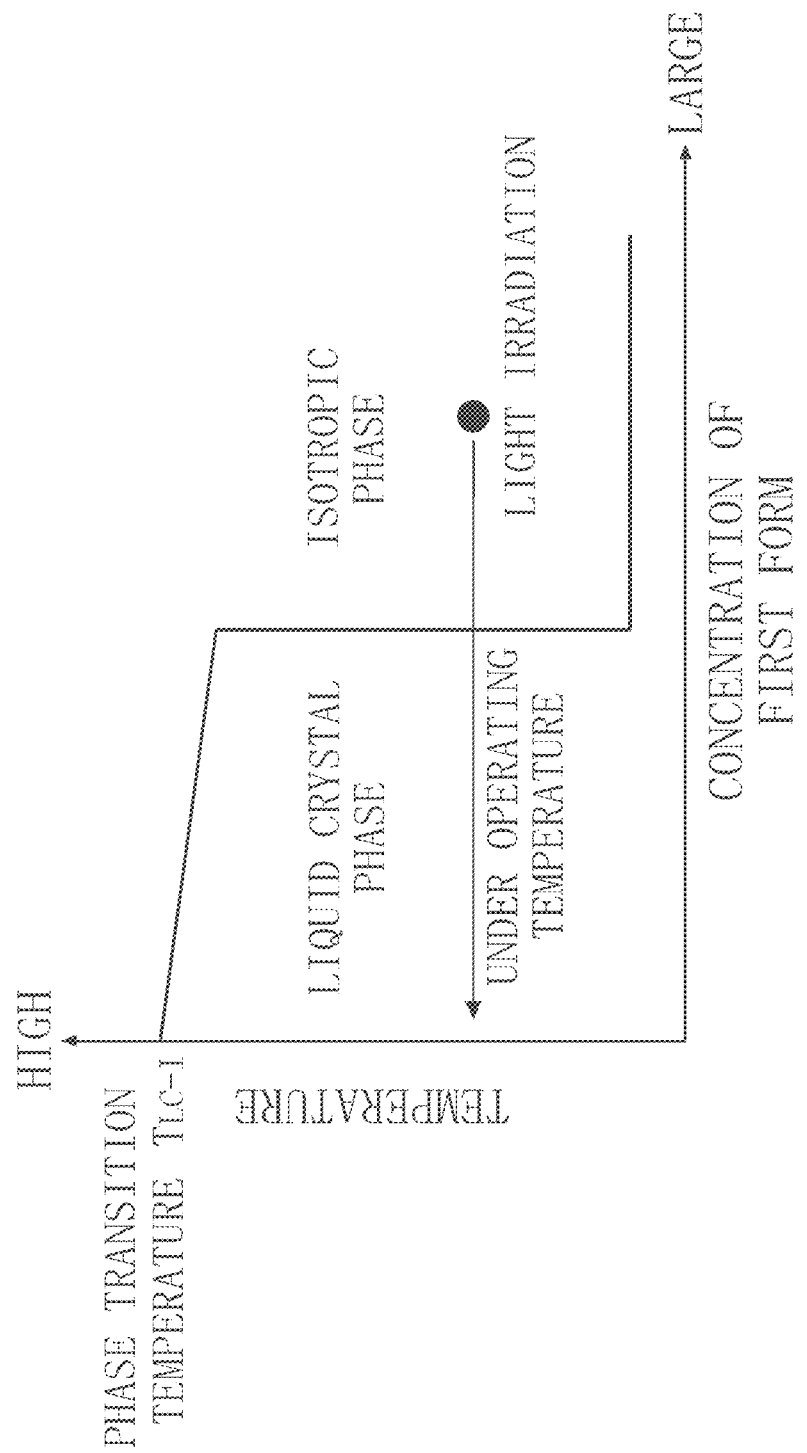
FIG. 7 is an explanatory diagram for explaining a change in phase transition temperature $T_{LC-1}$ associated with a reduction in concentration of a first form (cis isomer) associated with light irradiation.

(ii) In this photoresponsive liquid crystal material, first and second forms (cis isomer and trans isomer) are respectively formed by photoisomerization based on two different types of first and second irradiation lights. The concentration (ratio) of the first form and the concentration (ratio) of the second form have a relative relationship, and as the concentration of the first form increases, the concentration of the second form decreases. As shown in (FIG. 7), the first form has a function of reducing the phase transition temperature $T_{LC-1}$ as the concentration thereof increases as a state-change-related element. Therefore, in the photoresponsive liquid crystal material in the state of the isotropic phase, for example, when the phase transition temperature $T_{LC-1}$ is increased by reducing the concentration of the first form based on the second irradiation light, and the temperature (operating temperature) of the photoresponsive liquid crystal material becomes lower than the phase transition temperature $T_{LC\text{-}1}$, the phase transition to the liquid crystal phase occurs (see (FIG. 7)).

(iii) The function of the photoresponsive liquid crystal material is used for adhesion/peeling of the polymer compound (coating material) to/from the adhesion object. This will be described in detail. When the phase structure is in the isotropic phase, the photoresponsive liquid crystal material is in the state of the non-ordered liquid phase, and in this case, the polymer compound and the photoresponsive liquid crystal material are in a miscible state. Therefore, the photoresponsive liquid crystal material exists in the polymer compound without bleeding out on the outer surface of the polymer compound. On the other hand, when the phase structure is in the liquid crystal phase, the photoresponsive liquid crystal material is in the state of the ordered liquid phase, and in this case, the polymer compound and the photoresponsive liquid crystal material are in a phase separation state. Therefore, the photoresponsive liquid crystal material bleeds out (floats out) on the outer surface of the polymer compound (bleed-out phenomenon), and the photoresponsive liquid crystal material is interposed between (the outer surface of) the polymer compound and the adhesion object. Therefore, when the photoresponsive liquid crystal material does not bleed out on the outer surface of the polymer compound (non-syneresis state), the state of the photoresponsive liquid crystal material existing in the polymer compound is maintained, and the state of adhesion of the polymer compound to the adhesion object is maintained, and in contrast, when the photoresponsive liquid crystal material bleeds out on the outer surface of the polymer compound (syneresis state), the polymer compound is easily peeled from the adhesion object. Focusing on such a function of the photoresponsive liquid crystal material with respect to the polymer compound, the photoresponsive liquid crystal material is contained in the coating material.

(iv) The photoresponsive liquid crystal material has the phase structure set to the isotropic phase in advance by utilizing the first irradiation light of the first and second irradiation lights described above etc. This is because when the photoresponsive liquid crystal material, the polymerizable low-molecular-weight compound, and the polymerization initiator are mixed (in the state of the coating material), and the polymer compound is generated by the polymerization of the polymerizable low-molecular-weight compound so that the polymer compound is adhered to the adhesion object, the phase structure must be in the state of the isotropic phase. In other words, this is because the phase structure of the photoresponsive liquid crystal material is set to the isotropic phase to facilitate mixing of the polymerizable low-molecular-weight compound and the photoresponsive liquid crystal material, and based on the state of the isotropic phase, the photoresponsive liquid crystal material is prevented from causing the syneresis action to the polymer compound (decrease in adhesive strength is prevented). Therefore, especially in the latter case, when light irradiation is used for polymerization of the polymerizable low-molecular-weight compound, the first irradiation light (irradiation light for causing transition to the isotropic phase) is the same irradiation light as the irradiation light for polymerization so as to prevent the isotropic phase state of the photoresponsive liquid crystal material from transitioning to the liquid crystal phase due to the irradiation light for polymerization, and furthermore, considering the fact that the polymer compound adhered to the adhesion object is exposed to visible light in daily life, visible light is used for the first irradiation light and the irradiation light for the polymerization of the polymerizable low-molecular-weight compound. Specifically, for the irradiation light, when the phase structure of the photoresponsive liquid crystal material is changed from the liquid crystal phase to the isotropic phase, the visible light having a wavelength in the range of 400 to 600 nm is used, and the visible light having the wavelength of 405 nm is more preferably used. This is because the light of 405 nm is currently widely used as the light for curing a gel (coating material) in applications such as gel nails, and existing light sources can be used.

(v) When the polymer compound adhered to the adhesion object is peeled, the phase structure of the photoresponsive liquid crystal material is changed to the liquid crystal phase by using the light irradiation of the second irradiation light of the first and second irradiation lights described above. This is because by causing the syneresis action of the photoresponsive liquid crystal material to occur as described above for the polymer compound adhered to the adhesion object, not only the polymer compound is made peelable from the adhesion object, but also a person performiing the peeling treatment is prevented from being conscious of handling the peeling agent itself, and furthermore, the need for a pretreatment for performing the peeling treatment is eliminated.

(vi) In this embodiment, UV (ultraviolet) light is used as the second irradiation light (irradiation light causing transition from the isotropic phase to the liquid crystal phase). This is because unless the photoresponsive liquid crystal material in the polymer compound is irradiated with UV (ultraviolet) light that is special light in daily life, the phase structure of the photoresponsive liquid crystal material is maintained in the isotropic phase, and the syneresis action of the photoresponsive liquid crystal material is prevented from occurring for the polymer compound (decrease in adhesive strength of the polymer compound is prevented). In this embodiment, the UV (ultraviolet) light having a wavelength in the range of 300 to 400 nm is used, and the UV (ultraviolet) light having a wavelength of 365 nm is more preferably used. This is because the light source for the UV (ultraviolet) light is relatively easily available, and the UV (ultraviolet) light is actually widely used from the past as the light for curing a gel in applications such as gel nails. Furthermore, this is also because existing light sources currently still used in some cases are usable.

The intensity of the second irradiation light is appropriately selected depending on the photoresponsive liquid crystal material and the concentration thereof. The intensity is preferably 0.2 mW/cm$^2$ or more. This is because the intensity less than 0.2 mW/cm$^2$ cannot induce a photoisomerization reaction sufficient for causing a phase transition of the liquid crystal material. On the other hand, the upper limit of the intensity of the irradiation light is not particularly limited as long as no influence is exerted in consideration of the influence on the human body. However, from the viewpoint of practical preparation etc., 0.2 mW/cm$^2$ to 1000 mW/cm$^2$ (more preferably 1 to 100 mW/cm$^2$) is preferable.

(vii) Either an independent type photoresponsive liquid crystal material independently exhibiting a photoresponsive property and a liquid crystal property or a mixture type photoresponsive liquid crystal material composed of a mixture of a photoresponsive material and a liquid crystal material can be used as the photoresponsive liquid crystal material.

(vii-1) For the independent type photoresponsive liquid crystal material, a photoresponsive material exhibiting a liquid crystal property can be used. Examples of the usable material include an azobenzene compound etc. in which at least one of both ends of the azobenzene skeleton is substituted with an alkyl group or an alkoxy group and the other is substituted with an alkyl group, an alkoxy group, a cyano group, etc. This independent type photoresponsive liquid crystal material itself is photoisomerized into the first and second forms (cis isomer and trans isomer) based on two different types of the first and second irradiation lights, and the phase transition temperature $T_{LC-1}$ of the independent type photoresponsive liquid crystal material changes depending on the concentrations of the first and second forms. The phase state (liquid crystal phase or isotropic phase) is determined depending on whether the operating temperature of the independent type photoresponsive liquid crystal material is lower or higher than the phase transition temperature $T_{LC-1}$.

(vii-1-1) The independent type photoresponsive liquid crystal material is preferably in the range of 90 wt % to 10 wt % with respect to the entire coating material, more preferably 70 wt % to 30 wt % from the viewpoint of accurate phase separation from the polymer compound when the photoresponsive liquid crystal material is changed to the liquid crystal phase by the second irradiation light further preferably 60 wt % to 40 wt % from the viewpoint of maintaining the hardness of the film.

(vii-2) On the other hand, in the mixture type photoresponsive liquid crystal material, the photoresponsive material contained therein is photoisomerized into the first and second forms based on two different types of the first and second irradiation lights, and the phase transition temperature $T_{LC-1}$ of the mixture type photoresponsive liquid crystal material changes depending on the concentrations of the first and second forms. The phase state (liquid crystal phase or isotropic phase) is determined depending on whether the operating temperature of the mixture type photoresponsive liquid crystal material is lower or higher than the phase transition temperature $T_{LC-1}$.

(vii-2-1) Therefore, the photoresponsive material usable in such a mixture type photoresponsive liquid crystal material has, as is known, the basic skeleton structure that is, for example, an azobenzene structure, a spiropyran structure, a fulgide structure, a diarylethene structure, a salicylideneaniline structure, an anthracene structure, a norbornadiene structure, a cinnamoyl structure, a nitron structure, a benzaldoxime structure, a stilbene structure, a retinal structure, or an azomethine structure, and among them, preferable structures are the azobenzene structure and the stilbene structure causing a structural change of cis-trans isomerization due to light irradiation, and the spiropyran structure, the fulgide structure, or the diarylethene structure causing a ring-opening/ring-closing structural change due to light irradiation.

(vii-2-2) The liquid crystal material in the mixture type photoresponsive liquid crystal material may be any liquid crystal material as long as the phase transition occurs due to photoisomerization of the photoresponsive material; low-molecular-weight liquid crystals having biphenyl as well as terphenyl, phenylbenzoate, tolane, etc. known in the liquid crystal field are basically suitable from the viewpoint of a skeletal structure: all of the liquid crystal phase structures discovered so far are suitable from the viewpoint of the liquid crystal phase structure; and among them, the nematic phase, the smectic phase, the discotic phase, the cubic phase, and the cholesteric phase are particularly suitable. As described above, in the mixture type photoresponsive liquid crystal material, a desired material can be selected from many types of liquid crystal materials and many photoresponsive materials, so that a degree of freedom of selection can be increased as compared to the material independently exhibiting a photoresponsive property and a liquid crystal property. The mixture type photoresponsive liquid crystal material is composed of one or more types of the liquid crystal materials containing one or more types of the photoresponsive materials.

(vii-2-3) The mixture type photoresponsive liquid crystal material is preferably in the range of 90 wt % to 10 wt % with respect to the entire coating material, more preferably 70 wt % to 30 wt % from the viewpoint of accurate phase separation from the polymer compound when the photoresponsive liquid crystal material is changed to the liquid crystal phase by the second irradiation light further preferably 60 wt % to 40 wt % from the viewpoint of maintaining the hardness of the film.

(vii-2-4) The mass of the photoresponsive material relative to the sum of the mass of the liquid crystal material and the mass of the photoresponsive material in the mixture type photoresponsive material is preferably 10 wt % to 90 wt % a. The mass is more preferably 10 wt % to 70 wt % from the viewpoint of the solubility of the photoresponsive material with respect to the liquid crystal material, further preferably 20 wt % to 50 wt % from the viewpoint of the phase transition temperature $T_{LC-1}$ of the mixture type photoresponsive liquid crystal material determined by the operating temperature and the concentrations of the first and second forms.

(4) Therefore, if the coating material containing the peeling agent is used for coating of the adhesion object, this can create a situation in which the polymer compound can basically be adhered to the adhesion object although the photoresponsive liquid crystal material serving as the peeling agent is contained in the polymer compound, and on the other hand, the polymer compound can be peeled from the adhesion object (the photoresponsive liquid crystal material is bled out on the outer surface of the polymer compound) by simply bringing the photoresponsive liquid crystal material into the liquid crystal phase through photoisomerization based on light irradiation. Therefore, a person performing the peeling treatment can be prevented from being conscious of handling the peeling agent itself, and moreover, the pretreatment such as rubbing and scratching the surface of the polymer compound with a file can be omitted. Thus, when the polymer compound adhered to the adhesion object is peeled, a burden required for the peeling treatment can be reduced.

Moreover, in this case, basically regardless of what kind of the polymer compound is used, the photoresponsive liquid crystal material accurately exhibits the syneresis and non-syneresis actions with respect to the polymer compound, and therefore, a polymer compound can be selected from a number of types of polymer compounds with attention focused on the characteristics and applications thereof so as to select a polymerizable low-molecular-weight compound generating the polymer compound through polymerization. This can improve the reliability of adhesion etc. of the polymer compound to the adhesion object.

Specifically, in Patent Document 1 described above, a composition of a polymer compound (artificial nail) peelable with limonene serving as a peeling agent is described; however, limonene is contained in essential oils of lemon, orange, etc., and the polymer compound (artificial nail) may be peeled without intention of a user in daily life. In Patent Documents 2 and 3, compositions of polymer compounds (artificial nails) peelable with an acidic aqueous solution serving as a peeling agent are described; however, many acidic aqueous solutions exist as foods and beverages (lemon, Coke, dried plums, white wine, red wine, apples, vinegar, plum liquor, etc.), and even in this case, the polymer compound (artificial nail) may be peeled without intention of a user in daily life. However, when the coating material of the present invention is used, the selection of the polymer compound or the polymerizable low-molecular-weight compound is not limited, so that an appropriate polymer compound can be selected out of many polymer compounds in consideration of the characteristics related to adhesiveness etc. of the polymer compound, and a polymerizable low-molecular-weight compound producing the polymer compound through polymerization can be selected as a mixing element of the coating material. Furthermore, although a highly alkaline aqueous solution is described as a peeling agent in Patent Document 4, the highly alkaline aqueous solution may cause an irreversible action or a serious damage on the skin and eyes. However, the coating material of the preset invention contains a photoresponsive liquid crystal material as a peeling agent from the beginning, and it is not necessary to handle the peeling agent itself, so that the human body is not affected when the peeling treatment is performed.

2. The coating material (adhesive material) described above can be used as a main component of a gel for gel nails applied to nails and cured by light irradiation. The gel contains additives such as a buffer, a dispersant, a dye, a pigment, a preservative, and a thickener as needed, in addition to the polymerizable low-molecular-weight compound, the photopolymerization initiator, and the photoresponsive liquid crystal material serving as the coating material described above. In this case, the photoresponsive liquid crystal material in the gel is configured such that the phase structure is changed to the isotropic phase by visible light while the phase structure is changed to the liquid crystal phase by UV (ultraviolet) light, and in the gel state, the phase structure of the photoresponsive liquid crystal material is set to the isotropic phase in advance.

When the gel is used, the gel is placed and evenly spread on a human nail, and the gel is irradiated with visible light (e.g., 405 nm) by an LED lamp. As a result, the gel is cured, and the artificial nail (polymer compound) is formed on the human nail in a state of adhering to the surface of the human nail. In this case, the visible light is also applied to the photoresponsive liquid crystal material in the gel (artificial nail), however, since the phase structure of the photoresponsive liquid crystal material is changed to the isotropic phase by the visible light, the phase structure of the photoresponsive liquid crystal material is maintained in the isotropic phase, and the photoresponsive liquid crystal material does not bleed out on the outer surfaces (front surface and back surface) of the artificial nail. Therefore, even though the photoresponsive liquid crystal material is contained in the gel, the adhesiveness of the artificial nail to the human nail is not reduced.

To peel this artificial nail from the nail surface, the artificial nail is irradiated with UV (ultraviolet) light serving as the irradiation light. This irradiation with UV (ultraviolet) light causes transition of the phase structure of the photoresponsive liquid crystal material into the liquid crystal phase, so that the artificial nail and the photoresponsive liquid crystal material are brought into a phase separation state, and the photoresponsive liquid crystal material bleeds out to the outer surfaces (front surface and back surface) of the artificial nail. As a result, the photoresponsive liquid crystal material is interposed between the outer surface (back surface) of the artificial nail and a human nail surface, so that the artificial nail is made peelable from the human nail surface. Consequently, only the irradiation with UV (ultraviolet) light is required for performing the peeling treatment of the artificial nail, and the need for the pretreatment such as rubbing the artificial nail with a file to facilitate the permeation of the peeling agent can be eliminated.

3. The coating material (adhesive material) described above can be used as a paint (including floor wax). The paint contains additives suitable for the intended use of the paint as needed, in addition to the polymerizable low-molecular-weight compound, the photopolymerization initiator, and the photoresponsive liquid crystal material serving as the coating material described above. In this case, the conditions of the photoresponsive liquid crystal material in the paint are the same as the case of the gel nail described above.

When the paint is used, the paint is applied onto an application surface (floor surface, wall surface), and the paint on the application surface is heated to a predetermined temperature or higher at which polymerization of the paint on the application surface is started, or is irradiated with visible light (e.g., 405 nm) by using an LED lamp. As a result, the paint is cured, and a coating film is formed in a state of adhering to the application surface. When the curing with the visible light irradiation is used, the visible light is also applied to the photoresponsive liquid crystal material in the paint (coating film); however, since the phase structure of the photoresponsive liquid crystal material is changed to the isotropic phase by the visible light, the phase structure of the photoresponsive liquid crystal material is maintained in the isotropic phase, and the photoresponsive liquid crystal material does not bleed out on the outer surfaces (front surface and back surface) of the coating film. Therefore, even though the photoresponsive liquid crystal material is contained in the paint, the adhesiveness of the coating film to the application surface is not reduced.

When the coating film is soiled, the coating film can be peeled from the application surface. In this case, the coating film is irradiated with UV (ultraviolet) light serving as the irradiation light. This irradiation with UV (ultraviolet) light causes transition of the phase structure of the photoresponsive liquid crystal material into the liquid crystal phase, so that the coating film and the photoresponsive liquid crystal material are brought into a phase separation state, and the photoresponsive liquid crystal material bleeds out to the outer surfaces (front surface and back surface) of the coating film. As a result, the photoresponsive liquid crystal material is interposed between the outer surface (back surface) of the coating film and the application surface, so that the coating film is made peelable from the application surface. In this case, as the phase structure of the photoresponsive liquid crystal material transitions into the liquid crystal phase, the coating film becomes opaque from a transparent state, so that a region of bleeding out of the photoresponsive liquid crystal material to the outer surfaces (front surface and back surface) of the coating film can visually be confirmed. Consequently, only the irradiation with UV (ultraviolet) light is required for performing the peeling treatment of the coating film, and the need for the pretreatment such as rubbing the coating film with a file to facilitate the permeation of the peeling agent can be eliminated. Additionally, since the region of bleeding out of the photoresponsive liquid crystal material can visually be confirmed in the coating film, the peeling treatment can reliably be performed.

4. The adhesive material described above can be used as an adhesive for bonding an adhesion object and an object to be bonded. The adhesive contains additives suitable for the intended use of the adhesive as needed, in addition to the polymerizable low-molecular-weight compound, the photopolymerization initiator, and the photoresponsive liquid crystal material serving as the adhesive material described above. In this case, the conditions of the photoresponsive liquid crystal material in the adhesive are the same as the case of the gel nail described above.

When the adhesive is used, the adhesive is applied to at least one of the adhesion object and the object to be bonded, and the adhesion object and the object to be bonded are pressed against each other. Subsequently, one or more types of the polymerizable low-molecular-weight compounds in the adhesive are heated to a predetermined temperature or higher at which polymerization is started. As a result, the adhesive is cured, and the adhesion object and the object to be bonded are brought into a state of bonding via the polymer compound (adhesive layer). In this case, the phase structure of the photoresponsive liquid crystal material is maintained in the isotropic phase, so that the photoresponsive liquid crystal material does not bleed out between the polymer compound (adhesive layer) and the adhesion object and between the polymer compound (adhesive layer) and the object to be bonded. Therefore, even though the photoresponsive liquid crystal material is contained in the adhesive, the adhesiveness of the adhesive to the adhesion object and the object to be bonded is not reduced.

The polymer compound can be peeled from at least one of the adhesion object and the object to be bonded. In this case, the second irradiation light causing the phase structure of the photoresponsive liquid crystal material to transition from the isotropic phase to the liquid crystal phase is applied between the adhesion object and the object to be bonded (to a thickness surface), or at least one of the adhesion object and the object to be bonded is made up of a transparent member in advance, and the second irradiation light is applied through the transparent member to the photoresponsive liquid crystal material (the adhesive). Obviously, these two irradiation forms may be used together. As a result, even in this case, the photoresponsive liquid crystal material can be bled out to the outer surface of the polymer compound, and the polymer compound can be peeled from at least one of the adhesion object and the object to be bonded. Obviously, even in this case, the peeling agent itself is not consciously handled, and pretreatment is not required before the release treatment.

5. As a modification of each of the embodiments, a polymer compound itself may be dissolved instead of the polymerizable low-molecular-weight compound in a solvent and mixed with the photoresponsive liquid crystal material serving as the peeling agent to produce the coating material of the present invention. When this coating material is used, the coating material is applied to the adhesion object, and the solvent is then volatilized to cause the polymer compound to adhere to the adhesion object as a hard film. Obviously, even in this case, the photoresponsive liquid crystal material is contained in the coating material, and the non-syneresis action and the syneresis action of the photoresponsive liquid crystal material to the polymer compound are adjusted by light irradiation. In this case, solvents for dissolving the polymer compound and the photoresponsive liquid crystal material can widely be used as the solvent, and examples thereof include acetone, ethyl acetate, butyl acetate, and toluene. However, the present invention is not limited to these examples.

6. For the peeling agent of the present invention, a liquid crystal material (such as a liquid crystal material in the mixture type photoresponsive liquid crystal material described above) can be used on condition that the temperature is adjusted. This is because the non-syneresis and syneresis actions described above occur depending on a change in the phase structure of the liquid crystal material, and the phase structure of the liquid crystal material can be changed by making the temperature (operating temperature) of the liquid crystal material higher and lower than the phase transition temperature TLCi. Therefore, if a liquid crystal material (also in the isotropic phase) is used instead of the photoresponsive liquid crystal material in the adhesive material described above (obtained by polymerizing the polymerizable low-molecular-weight compound or by volatilizing the solvent from the polymer compound dissolved in the solvent), the polymer compound can adhere to the adhesion object and/or the object to be bonded, and by making the operating temperature of the liquid crystal material lower than the phase transition temperature $T_{LC-1}$ after the adhesion, the liquid crystal material is brought into the liquid crystal phase, so that the liquid crystal material exhibits the syneresis action to the polymer compound. As a result, the polymer compound can be peeled from the adhesion object and/or the object to be bonded.

From the above, even when the adhesive material is used as the adhesive bonding the adhesion object and the object to be bonded, for example, even when a floor surface and carpets or a wall surface and interior wall materials are bonded to each other, the carpets and the interior wall materials can easily be peeled from the adhesion object (the floor surface, the wall surface). This is because when the operating temperature of the liquid crystal material is made lower than the phase transition temperature $T_{LC-1}$ by using a cooling material such as dry ice to bring the phase structure into the liquid crystal phase, the syneresis action of the liquid crystal material is exhibited.

EXAMPLES

7. Specific experimental examples will hereinafter be described.

First, photopolymerizable mixtures 1 to 3 and photosyneresis liquid peeling agents 1, 2 were prepared as follows.

Preparation of Photopolymerizable Mixture 1

The photopolymerizable mixture 1 was prepared by mixing Poly(ethylene glycol) methyl ether methacrylate (4.95 wt %), isobornyl methacrylate (4.95 wt %), diurethane dimethacrylate (89.1 wt %), and phenylbis(2,4,6-trimethylbenzoyl)phosphine oxide (1 wt %).

Preparation of Photopolymerizable Mixture 2

The photopolymerizable mixture 2 was prepared by mixing poly(ethylene glycol) methyl ether methacrylate (4.95 wt %), isobornyl methacrylate (9.9 wt %), bisphenol A ethoxylate diacrylate (84.15 wt %), and phenylbis(2,4,6-trimethylbenzoyl)phosphine oxide (1 wt %).

Preparation of Photopolymerizable Mixture 3

The photopolymerizable mixture 3 was prepared by mixing poly(ethylene glycol) methyl ether methacrylate (5.22 wt %), isobornyl methacrylate (10.01 wt %), 2-phenoxyethyl methacrylate (5.21 wt %), bisphenol A ethoxylate diacrylate (78.52 wt %), phenylbis(2,4,6-trimethylbenzoyl)phosphine oxide (1.04 wt %).

Preparation of Photo-Syneresis Liquid Peeling Agent 1

The photo-syneresis liquid peeling agent 1 was prepared by mixing 4-pentyl-4'-cyanobiphenyl (25.6 wt %), 4-hexyloxy-4'-cyanobiphenyl (25.6 wt %), 4-decyloxy-4'-cyanobiphenyl (24.1 wt %), cis-4-methylstilbene (22.5 wt %), and benzophenone (2.2 wt %).

Preparation of Photo-Syneresis Liquid Peeling Agent 2

The photo-syneresis liquid peeling agent 2 was prepared by mixing 4-(trans-4-amylcyclohexyl)benzonitrile (82 wt %), cis-4-methylstilbene (16.4 wt %), and benzophenone (1.6 wt %).

The following experiments were conducted by using the photopolymerizable mixtures 1 to 3 and the photo-syneresis liquid peeling agents 1, 2.

Example 1

When a composition composed of the photopolymerizable mixture 1 (50 wt %) and the photo-syneresis liquid peeling agent 1 (50 wt %) was irradiated with visible light (wavelength=405 nm, intensity=30 mW/cm$^2$) at 25° C. for 3 minutes for light curing, a pale white transparent resin was obtained, and the syneresis of the photo-syneresis liquid peeling agent was not confirmed (the resin on the left side of (FIG. 1) (hereinafter referred to as a pre-photo-syneresis resin in Example 1)). When the pre-photo-syneresis resin was irradiated with UV (ultraviolet) light (wavelength=365 nm, intensity=150 mW/cm$^2$) at 25° C. for 10 minutes, the resin became more clouded and the photo-syneresis liquid peeling agent bled out on the resin surface (the resin on the right side of (FIG. 1) (hereinafter referred to as a post-photo-syneresis resin in Example 1)).

Figure 2:
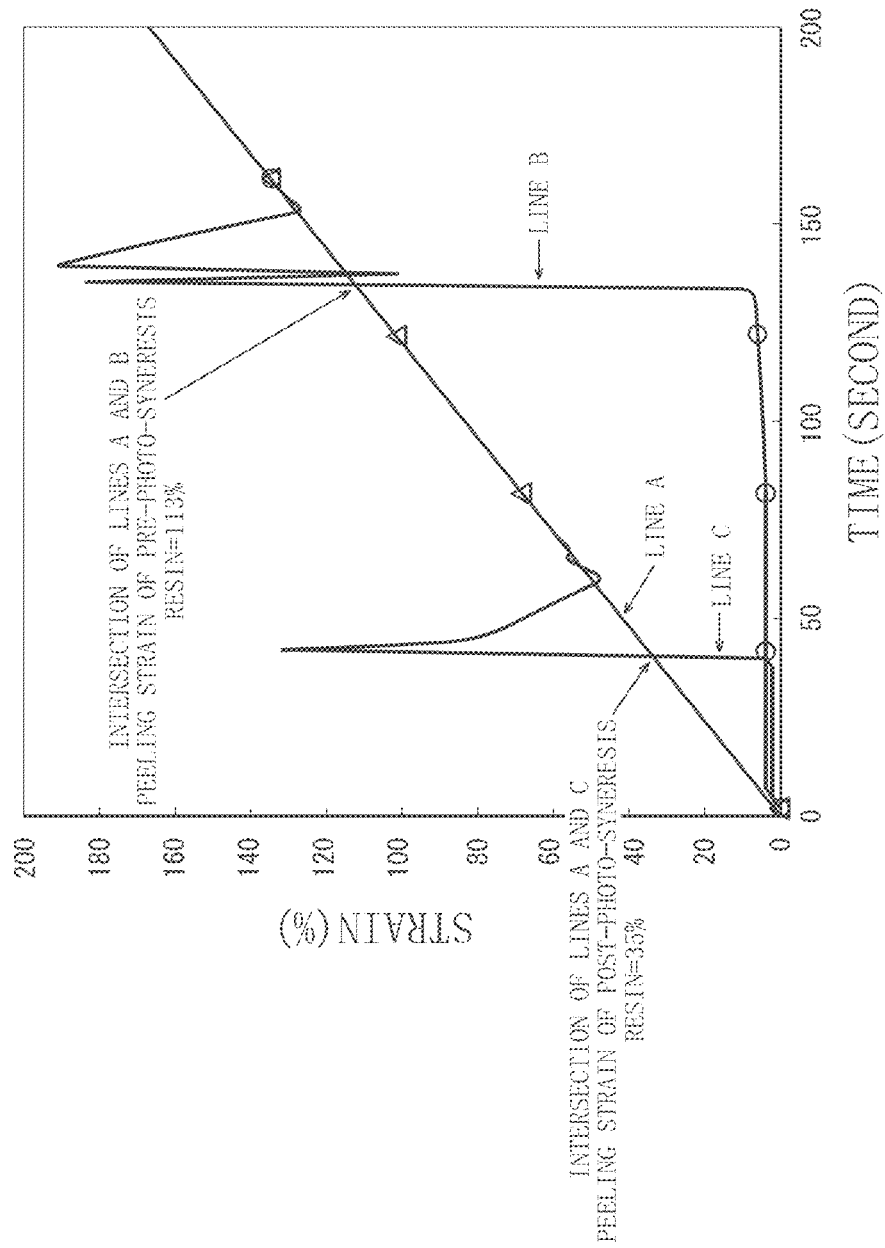
FIG. 2 is a diagram showing adhesion properties (peeling properties) of the resins obtained from the composition composed of the photopolymerizable mixture 1 and the photo-syneresis liquid peeling agent 1, before photo-syneresis (pre-photo-syneresis resin) and after photo-syneresis (post-photo-syneresis resin).

The adhesiveness of the resins before and after photo-syneresis was evaluated by using a rheometer (MCR302, Anton-Paar). When the composition was placed between a glass stage and a measuring jig with a gap set to 2 mm and the pre-photo-syneresis resin was prepared under the conditions described above to perform measurement with a program of increasing a lateral strain applied to the resin (a rate relative to thickness) at a frequency of 1 Hz from 0.1% to 500% linearly over time (line A of (FIG. 2)), the pre-photo-syneresis resin (line B of (FIG. 2)) firmly adhered to the measuring jig almost without movement of the jig until the strain corresponding to 113% of the sample thickness; however, when the strain became larger than that corresponding to 113% of the sample thickness, the measuring jig came off from the resin (intersection of lines A and B of (FIG. 2)). When the composition was placed in the rheometer again and the post-photo-syneresis resin was prepared under the conditions described above to perform measurement with the program of increasing a lateral strain applied to the resin (a rate relative to thickness) at a frequency of 1 Hz from 0.1% to 500% linearly over time (line A), the post-photo-syneresis resin (line C of (FIG. 2)) firmly adhered to the measuring jig almost without movement of the jig until the strain corresponding to 35% of the sample thickness, however, when the strain became larger than that corresponding to 35% of the sample thickness, the measuring jig came off from the resin (intersection of lines A and C of (FIG. 2)), and it was confirmed that the resin was peelable by applying a smaller strain due to photo-syneresis.

Example 2

Figure 3:
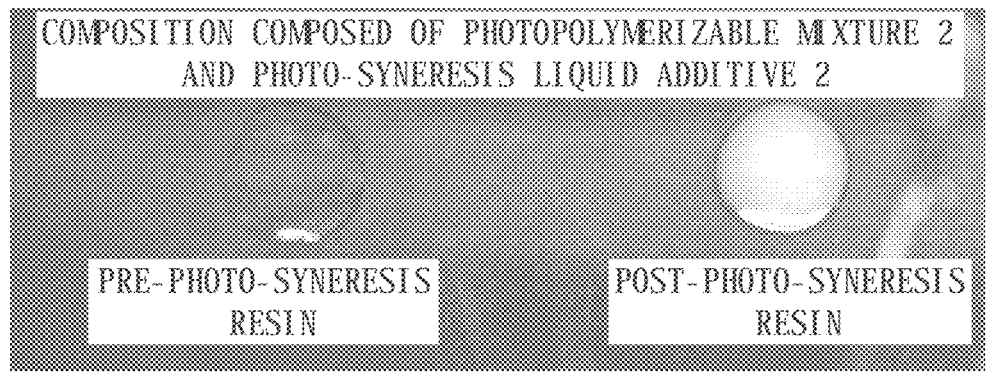
FIG. 3 is a photographic diagram showing a state of resins obtained from a composition composed of a photopolymerizable mixture 2 and a photo-syneresis liquid peeling agent 2, before photo-syneresis (pre-photo-syneresis resin) and after photo-syneresis (post-photo-syneresis resin).

When a composition composed of the photopolymerizable mixture 2 (50 wt %) and the photo-syneresis liquid peeling agent 2 (50 wt %) was irradiated with visible light (wavelength=405 nm, intensity=30 mW/cm$^2$) at 25° C. for 3 minutes for light curing, a colorless transparent resin was obtained, and the syneresis of the photo-syneresis liquid peeling agent was not confirmed (the resin on the left side of (FIG. 3) (hereinafter referred to as a pre-photo-syneresis resin in Example 2)). When the pre-photo-syneresis resin was irradiated with UV (ultraviolet) light (wavelength=365 nm, intensity=150 mW/cm$^2$) at 25° C. for 10 minutes, the resin became clouded and the photo-syneresis liquid additive bled out on the resin surface (the resin on the right side of (FIG. 3) (hereinafter referred to as a post-photo-syneresis resin in Example 2))

Figure 4:
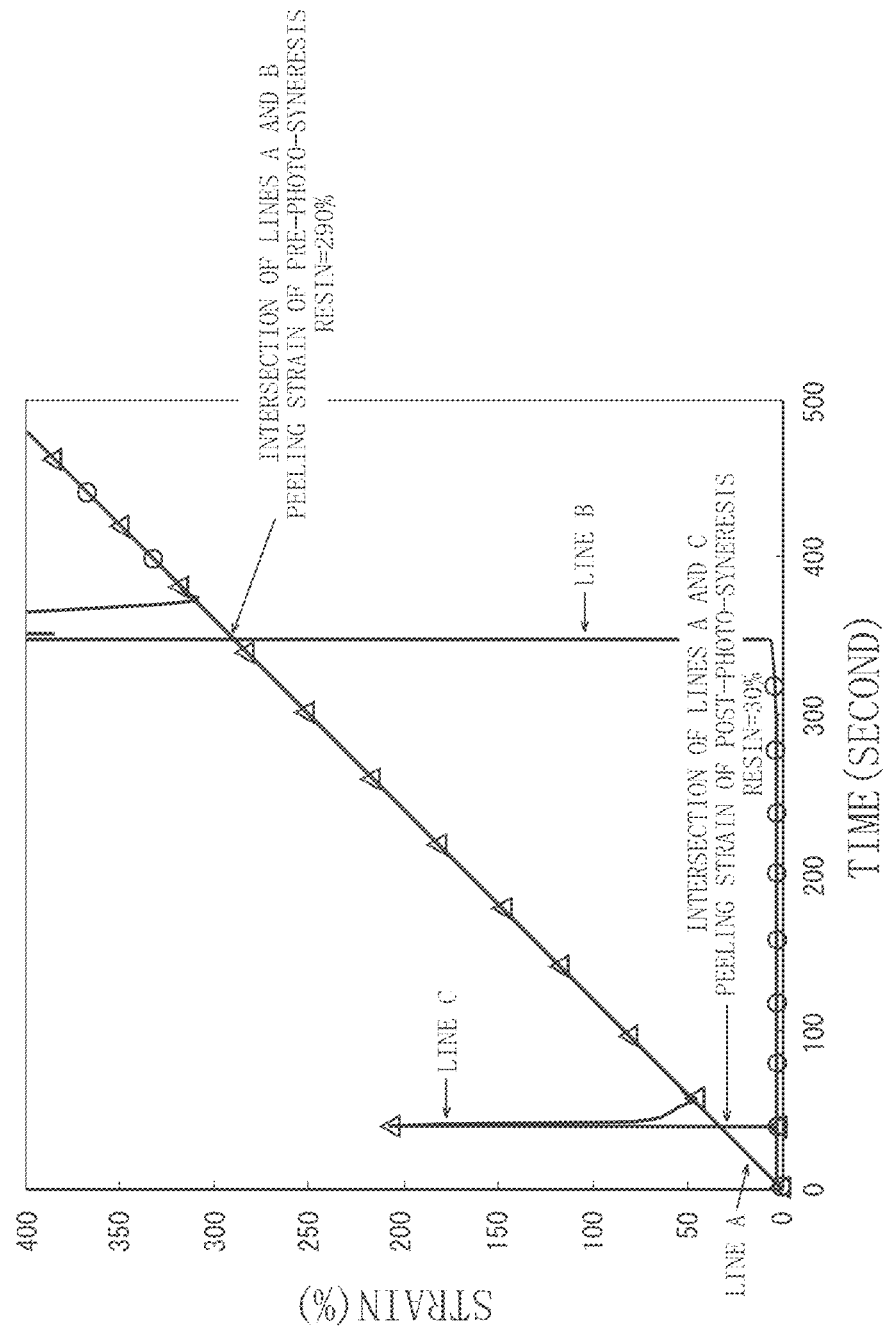
FIG. 4 is a diagram showing adhesion properties (peeling properties) of the resins obtained from the composition composed of the photopolymerizable mixture 2 and the photo-syneresis liquid peeling agent 2, before photo-syneresis (pre-photo-syneresis resin) and after photo-syneresis (post-photo-syneresis resin).

The adhesiveness of the resins before and after photo-syneresis was evaluated by using a rheometer (MCR302, Anton-Paar). When the composition was placed between a glass stage and a measuring jig with a gap set to 2 mm and the pre-photo-syneresis resin was prepared under the conditions described above to perform measurement with a program of increasing a lateral strain applied to the resin (a rate relative to thickness) at a frequency of 1 Hz from 0.1% to 500% linearly over time (line A of (FIG. 4)), the pre-photo-syneresis resin (line B of (FIG. 4)) firmly adhered to the measuring jig almost without movement of the jig until the strain corresponding to 290% of the sample thickness; however, when the strain became larger than that corresponding to 290% of the sample thickness, the measuring jig came off from the resin (intersection of lines A and B of (FIG. 4)). When the composition was placed in the rheometer again and the post-photo-syneresis resin was prepared under the conditions described above to perform measurement with the program of increasing a lateral strain applied to the resin (a rate relative to thickness) at a frequency of 1 Hz from 0.1% to 500% linearly over time (line A), the post-photo-syneresis resin (line C of (FIG. 4)) firmly adhered to the measuring jig almost without movement of the jig until the strain corresponding to 30% of the sample thickness; however, when the strain became larger than that corresponding to 30% of the sample thickness, the measuring jig came off from the resin (intersection of lines A and C of (FIG. 4)), and it was confirmed that the resin was peelable by applying a smaller strain due to photo-syneresis.

Example 3

Figure 5:
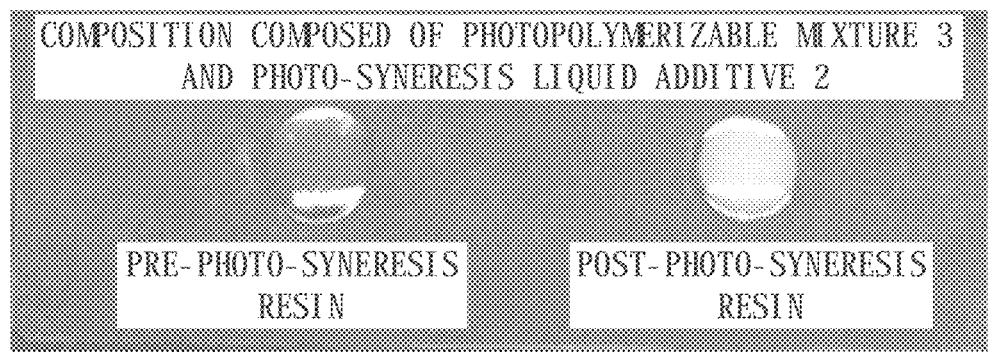
FIG. 5 is a photographic diagram showing a state of resins obtained from a composition composed of a photopolymerizable mixture 3 and a photo-syneresis liquid peeling agent 3, before photo-syneresis (pre-photo-syneresis resin) and after photo-syneresis (post-photo-syneresis resin).

When a composition composed of the photopolymerizable mixture 3 (50 wt %) and the photo-syneresis liquid peeling agent 2 (50 wt %) was irradiated with visible light (wavelength=405 nm, intensity=30 mW/cm$^2$) at 25° C. for 3 minutes to light-cure the composition, a colorless transparent resin was obtained, and the syneresis of the photo-syneresis liquid additive was not confirmed (the resin on the left side of (FIG. 5) (hereinafter referred to as a pre-photo-syneresis resin in Example 3)). When the pre-photo-syneresis resin was irradiated with UV (ultraviolet) light (wavelength=365 nm, intensity=150 mW/cm$^2$) at 25° C. for 10 minutes, the resin became clouded and the photo-syneresis liquid peeling agent bled out on the resin surface (the resin on the right side of (FIG. 5) (hereinafter referred to as a post-photo-syneresis resin in Example 3)).

The adhesiveness of the resins before and after photo-syneresis was evaluated by using a rheometer (MCR302, Anton-Paar). When the composition was placed between a glass stage and a measuring jig with a gap set to 2 mm and the pre-photo-syneresis resin was prepared under the conditions described above to perform measurement with a program of increasing a lateral strain applied to the resin (a rate relative to thickness) at a frequency of 1 Hz from 0.1% to 500% linearly over time (line A of (FIG. 6)), the pre-photo-syneresis resin (line B of (FIG. 6)) firmly adhered to the measuring jig almost without movement of the jig until the strain corresponding to 255% of the sample thickness; however, when the strain became larger than that corresponding to 255% of the sample thickness, the measuring jig came off from the resin (intersection of lines A and B of (FIG. 6)). When the composition was placed in the rheometer again and the post-photo-syneresis resin was prepared under the conditions described above to perform measurement with the program of increasing a lateral strain applied to the resin (a rate relative to thickness) at a frequency of 1 Hz from 0.1% to 500% linearly over time (line A), the post-photo-syneresis resin (line C of (FIG. 6)) firmly adhered to the measuring jig almost without movement of the jig until the strain corresponding to 90% of the sample thickness; however, when the strain became larger than that corresponding to 90% of the sample thickness, the measuring jig came off from the resin (intersection of lines A and C of (FIG. 6)), and it was confirmed that the resin was peelable by applying a smaller strain due to photo-syneresis.

Although the embodiments have been described above, in the present invention, the adhesive material is not limited to the coating material and the adhesive and is usable in various applications as long as the polymer compound having adhered to the adhesion object can be peeled.

INDUSTRIAL APPLICABILITY

The peeling agent and the coating material of the present invention can be used for gels(for gel nails), paints, adhesives, etc.

The invention claimed is:

1. A method for peeling a polymer compound having adhered to an adhesion object, comprising:
preparing an adhesive material by mixing one or more types of polymerizable low-molecular-weight compounds, a polymerization initiator, and a photoresponsive liquid crystal material having a phase structure in an isotropic phase state;
adhering the adhesive material to the adhesion object, and generating the polymer compound by polymerizing the one or more types of the polymerizable low-molecular-weight compounds after the adhesive material is placed on the adhesion object;
photoisomerizing based on the light irradiation so that the phase structure of the photoresponsive liquid crystal material is changed from the isotropic phase to the liquid crystal phase; and
peeling the polymer compound from the adhesion object when the photoresponsive liquid crystal material bleeds out on the outer surface of the polymer compound.

2. The method according to claim 1, wherein
the adhesive material is a main component of a gel for a gel nail, and wherein
the adhesion object is a human nail.

3. The method according to claim 1, wherein
the adhesive material is a main component of a paint, and wherein
the adhesion object is an application surface.

4. The method according to claim 1, wherein
when an object to be bonded is bonded to the adhesion object via the adhesive material, after the adhesive material is applied to at least one of the adhesion object and the object to be bonded, the adhesion object and the object to be bonded are pressed against each other to generate the polymer compound between the adhesion object and the object to be bonded, and wherein
when the polymer compound is peeled from at least one of the adhesion object and the object to be bonded, an irradiation light for transitioning the phase structure of the photoresponsive liquid crystal material from the isotropic phase to the liquid crystal phase is applied between the adhesion object and the object to be bonded, or after at least one of the adhesion object and the object to be bonded is made up of a transparent member in advance, the irradiation light is applied to the transparent member, wherein the irradiation light is applied to the transparent member to cause the photoresponsive liquid crystal material to bleed out on the outer surface of the polymer compound.

5. A method for peeling a polymer compound having adhered to an adhesion object, wherein comprising:
preparing an adhesive material that contains a solvent, a polymer compound dissolved in the solvent and becoming adhesive while forming a film on an adhesion object when the solvent volatilizes, and a photoresponsive liquid crystal material mixed with the polymer compound in the solvent with the phase structure set to an isotropic phase;
adhering the adhesive material to the adhesion object, the solvent being volatilized after the adhesive material is placed on the adhesion object;
photoisomerizing based on the light irradiation so that the phase structure of the photoresponsive liquid crystal material is changed from the isotropic phase to the liquid crystal phase; and
peeling the polymer compound from the adhesion object when the photoresponsive liquid crystal material bleeds out on the outer surface of the polymer compound.

6. The method according to claim 5, wherein
the adhesive material is a main component of a gel for a gel nail, and wherein
the adhesion object is a human nail.

7. The method according to claim 5, wherein
the adhesive material is a main component of a paint, and wherein
the adhesion object is an application surface.

8. The method according to claim 5, wherein
when an object to be bonded is bonded to the adhesion object via the adhesive material, after the adhesive material is applied to at least one of the adhesion object and the object to be bonded, the adhesion object and the object to be bonded are pressed against each other to generate the polymer compound between the adhesion object and the object to be bonded, and wherein
when the polymer compound is peeled from at least one of the adhesion object and the object to be bonded, an irradiation light for transitioning the phase structure of the photoresponsive liquid crystal material from the isotropic phase to the liquid crystal phase is applied between the adhesion object and the object to be bonded, or after at least one of the adhesion object and the object to be bonded is made up of a transparent member in advance, the irradiation light is applied to the transparent member, wherein the irradiation light is applied to the transparent member to cause the photoresponsive liquid crystal material to bleed out on the outer surface of the polymer compound.

* * * * *